United States Patent [19]

Phillips et al.

[11] 4,179,926

[45] Dec. 25, 1979

[54] MULTIPLE SIGNAL THERMOPARTICULATING COATING

[75] Inventors: David C. Phillips; William M. Hickam, both of Pittsburgh; James D. B. Smith, Turtle Creek, all of Pa.

[73] Assignee: Westinghouse Electric Corp., Pittsburgh, Pa.

[21] Appl. No.: 796,242

[22] Filed: May 12, 1977

Related U.S. Application Data

[63] Continuation-in-part of Ser. No. 568,218, Apr. 15, 1975.

[51] Int. Cl.$^2$ .............. C09K 3/00; G08B 21/00; G01K 13/00; G01K 1/00; G01K 3/04; G01K 3/08

[52] U.S. Cl. .................... 73/339 R; 73/23; 73/28; 73/349; 252/408; 310/55; 310/56

[58] Field of Search ....... 252/408; 73/339 R, 339 TP, 73/23, 28, 349; 310/55, 56

[56] References Cited

U.S. PATENT DOCUMENTS

| | | | |
|---|---|---|---|
| 3,329,022 | 7/1967 | Feldman | 73/339 R |
| 3,427,880 | 2/1969 | Crobel et al. | 73/339 R |
| 3,955,417 | 5/1976 | Smith et al. | 73/339 R |
| 3,957,014 | 5/1976 | Phillips et al. | 116/114 F |
| 3,973,438 | 8/1976 | Smith et al. | 73/339 R |
| 3,973,439 | 8/1976 | Smith et al. | 73/339 R |
| 3,979,353 | 9/1976 | Smith et al. | 73/339 R |
| 3,995,489 | 12/1976 | Smith et al. | 73/339 R |
| 4,046,733 | 9/1977 | Smith et al. | 73/339 R |
| 4,046,943 | 9/1977 | Smith et al. | 73/339 R |
| 4,056,005 | 11/1977 | Smith et al. | 73/339 R |
| 4,056,006 | 11/1977 | Smith et al. | 73/339 R |
| 4,074,137 | 2/1978 | Carson et al. | 73/339 R |

OTHER PUBLICATIONS

Pietsch, H. E., et al., "Sacrificial coatings for improved detection of overheating in generators," IEEE PES winter meeting, N.Y., N.Y., (Feb. 4, 1977).

Fort, E. M., et al, "Detection and identification of overheating components of electrical generators," IEEE-ASME, Miami, Fla., (Sep. 19, 1974).

Sexton, R. M., et al., "Chemical monitoring of hydrogen-cooled turbine generators brought up to date," 42nd annual conf. of Doble clients, Boston, Mass. (Apr. 1975).

*Primary Examiner*—Benjamin R. Padgett
*Assistant Examiner*—T. S. Gron
*Attorney, Agent, or Firm*—R. D. Fuerle

[57] ABSTRACT

A composition is disclosed of a solution of a resinous carrier and at least two compounds which thermoparticulate at different temperatures between 60° and 200° C. A coating is made by applying the composition to a portion of an electrical apparatus exposed to a gas stream. As the temperature of the coating increases the compounds therein thermoparticulate. The time between which the compounds thermoparticulate indicates the rate of rise of the temperature and analysis of the products of thermoparticulation indicates the location of the coating in the electrical apparatus. Alternatively, the coating can consist of several layers with a thermoparticulating compound in each layer which thermoparticulates at different temperatures.

20 Claims, No Drawings

MULTIPLE SIGNAL THERMOPARTICULATING COATING

CROSS-REFERENCES TO RELATED APPLICATIONS

This application is a continuation-in-part of copending application Ser. No. 568,218 filed Apr. 15, 1975.

This application is related to application Ser. No. 426,391 filed Dec. 19, 1973 by Emil M. Fort, Thomas D. Kaczmarek, and David Colin Phillips titled "Sampling System For Power Generators," now U.S. Pat. No. 3,972,225.

This application is also related to application Ser. No. 568,221, filed of even date, by J. D. B. Smith and D. C. Phillips titled "Metal Acetyl Acetonate Composition For Forming Thermoparticulating Coating," now U.S. Pat. No. 3,973,439.

This application is related to application Ser. No. 568,219, filed of even date by J. D. B. Smith and D. C. Phillips titled "Malonic Acid Derivative Composition For Forming Thermoparticulating Coating," now U.S. Pat. No. 3,995,489.

This application is related to application Ser. No. 390,284, filed Aug. 21, 1973 by J. D. B. Smith and D. C. Phillips titled "Malonic Acid Composition For Thermoparticulating Coating," now U.S. Pat. No. 3,973,438.

This application is related to application Ser. No. 568,224, filed of even date by J. D. B. Smith and D. C. Phillips titled "Diazonium Salt Composition For Forming Thermoparticulating Coating," now U.S. Pat. No. 3,979,353.

This application is related to application Ser. No. 568,223, filed of even date by J. D. B. Smith, D. C. Phillips and K. W. Grossett titled "Grease Thermoparticulating Coating," now U.S. Pat. No. 3,955,417.

This application is related to application Ser. No. 568,222, filed of even date by J. D. B. Smith, J. F. Meier and D. C. Phillips titled "Blocked Isocyanate Composition For Forming Thermoparticulating Coating," now U.S. Pat. No. 4,056,005.

BACKGROUND OF THE INVENTION

Electrical apparatus, such as motors and turbine generators, occasionally overheat due to shorts or other malfunctions. The longer the overheating continues the more damage is done to the apparatus. A malfunction detected immediately may mean only a quick repair but if the overheating continues, the entire machine may be damaged.

Large rotating electrical apparatus is usually cooled with a hydrogen gas stream. The organic compounds in the apparatus are first to be affected by the overheating and they decompose to form particles which enter the gas stream. Monitors then detect particles in the gas stream and sound a warning or shut down the apparatus when too many particles are detected.

Descriptions of such monitors and how they function may be found in U.S. Pat. No. 3,427,880 titled "Overheating Detector For Gas Cooled Electrical Machine" and in U.S. Pat. No. 3,573,460 titled "Ion Chamber For Submicron Particles." Another monitor, "The Condensation Nuclei Detector," is described by F. W. Van-Luik, Jr. and R. E. Rippere, in an article titled "Condensation Nuclei, A New Technique For Gas Analysis," in Analytical Chemistry 34, 1617 (1962) and by G. F. Skala, in an article titled "A New Instrument For The Continuous Detection Of Condensation Nuclei," in Analytical Chemistry 35, 702 (1963).

As U.S. Pat. Nos. 3,427,880 and 3,807,218, and the hereinbefore-cited cross-referenced applications disclose, special coatings may be applied to the apparatus which decompose to form detectable particles (i.e., thermoparticulate) at a lower temperature than the usual organic compounds found in the apparatus. However, merely knowing that an area in the generator is being overheated may not be enough information on which to base a decision to shut down the generator. Since shutting down a generator means the loss of the electricity which would have been generated plus the cost of inspecting, disassembling, and reassembling the generator, such decisions are not made lightly.

SUMMARY OF THE INVENTION

We have discovered that the rate at which the temperature rises in a particular area of a generator can be determined by applying to a surface in the gas stream of the generator a coating which contains at least two compounds which thermoparticulate at different temperatures between 60° and 200° C. If the rate of temperature increase is rapid, a runaway situation is probably occurring and the generator must be shut down. On the other hand, if the temperature rise is slow, the load on the generator can be reduced while the generator is checked and analyzed. Also, because various combinations of thermoparticulating compounds can be used in the coating, the location of the overheating in the generator can be determined by analyzing the products of thermoparticulation. The location of overheating can also be determined visually because the thermoparticulating compounds described herein (except for the grease) blister and darken when they decompose.

DESCRIPTION OF THE INVENTION

A composition is prepared of at least two thermoparticulating compounds (hereinafter "TPC's") in a solution of a resinous carrier. The TPC may be dispersed if they are insoluble in the solvent (e.g., toluene) or they may be in solution if they are soluble in the solvent (e.g., ethyl alcohol or diethyl ether). Dispersions are preferred as they produce much more particulation than do solutions. A particle size of the dispersed TPC's of about 25 to about 1000 microns is suitable.

A suitable composition is a resinous carrier, about 20 to about 250 phr (parts by weight per hundred parts of resinous carrier not including solvent) total of the TPC's and about 25 to about 75% (by weight based on the resinous carrier) of a solvent for the resinous carrier. If the total amount of the TPC is less than about 20 phr, the quantity of particles given off during decomposition may be too low to be detected by presently-existing detectors. However, the construction of more sensitive detectors would permit a lower amount of TPC. If the amount of TPC exceeds about 250 phr, the composition is thick, difficult to apply, and does not bond well. The preferred amount of TPC, which generally gives the best results, is about 40 to about 60 phr. If the amount of solvent is less than about 25%, the composition is generally too viscous to apply easily and if the amount of solvent is greater than 75%, the composition is unnecessarily dilute and the coating may be too thin to produce an adequate number of particles during decomposition, at least while the malfunction is highly localized. Best results are usually obtained with about 45 to about 55% solvent.

The resinous carrier performs the function of bonding the TPC to the apparatus since a coating of a TPC by itself does not adhere well. The resinous carrier should be compatible with the other resins used in the apparatus and therefore it is usually advantageous to use the same resin used elsewhere. The resinous carrier is curable at 60° C., and is preferable air-dryable since it cannot be easily cured in place with heat. Also, it should be stable after curing for several years at 60° C. The resin must be unreactive with the TPC for otherwise suitable thermoparticulation will not occur. The TPC and the resin from a mixture and the TPC does not catalyze the cure of the resin. Epoxy resins are preferred as they are usually used elsewhere in the apparatus, but polyester, silicone rubber, styrene, etc. could also be used.

The solvent for the resinous carrier depends on the particular resinous carrier used. Toluene, xylene, benzene, methyl ethyl ketone, ethyl alcohol, diethyl ether, acetone, cellosolve, etc. are common solvents that may be used. Toluene is preferred as it is inexpensive and dissolves most resins.

The composition also preferably contains about 0.1 to about 3 phr of a drier when the resinous carrier is an epoxy resin or similar resin, to promote its room temperature cure. Lead naphthenate or cobalt naphthenate is preferred although stannous octoate, zinc stearate, etc. could also be used. Resins such as polyesters may also require the presence of an organic peroxide as is known in the art. Mixtures of various resins, solvents, or driers are also contemplated.

The composition may be prepared by simply mixing the ingredients, but it is preferable to mix the drier, resinous carrier, and solvent first and then add the TPC to prevent the occlusion of the drier in the TPC and thereby to obtain a more homogeneous dispersion of the TPC. Certain TPC's, such as the greases described herein, can be applied directly and need not be mixed into a composition with a solvent and resinous carrier.

The TPC's of this invention are compounds which are stable solids or greases at 50° C., but which decompose at 60° to 200° C. to produce detectable particles. With presently-existing monitors particles must be larger than about 25 Å in order to be detected, but future monitors may be capable of detecting smaller particles. The previously cross-referenced applications, herein incorporated by reference, describe many suitable TPC's. Briefly, these compounds include diazonium salts, malonic acid and its derivatives, metal acetyl acetonates, blocked isocyanates, and certain greases. The following tables are lists of useful thermoparticulating compounds from those previously cross-referenced applications.

| Metal Acetylacetonate | Days Aged At 60° C. | Thermoparticulating Temperature Range (°C.) |
|---|---|---|
| $Zn(C_5H_7O_2) \cdot 2H_2O$ | 110 | 95–100 |
| $Al(C_5H_7O_2)_3$ | 44 | 159–161 |
| $Fe(C_5H_7O_2)_3$ | 6 | 171–174 |
| $Mg(C_5H_7O_2)_2 \cdot 2H_2O$ | 6 | 192–195 |
| $Mn(C_5H_7O_2)_3$ | 1 | 132–133 |
| $Mn(C_5H_7O_2)_2$ | 1 | 182–185 |
| $Co(C_5H_7O_2)_2$ | 1 | 128–131 |
| $Co(C_5H_7O_2)_3$ | 1 | 150–152 |
| $Co(C_5H_7O_2)_2 \cdot H_2O$ | 1 | 165–168 |
| $Cr(C_5H_7O_2)_3$ | 1 | 179–183 |
| $Ni(C_5H_7O_2)_2 \cdot 2H_2O$ | 1 | 169–173 |

| Grease | Aging Time at 120° C. (days) | | |
|---|---|---|---|
|  | 3 | 59 | 84 |
| A mixture of about 20% telomer of polytetrafluoroethylene and about 80% perfluoroalkyl polyether, sold by DuPont under the trademark "Krytox 240-AD" | 194°–198° C. | 191°–198° C. | 200°–207° C. |

The above table gives the thermoparticulation temperature after various periods of aging.

| Diazonium Salt | Literature Decomposition Temperature (°C.) | Support Material | Concentration in Epoxy (phr)[b] | Additional Heat Treatment | Thermoparticulation Temperature (°C.) |
|---|---|---|---|---|---|
| 3-chloro-4-diethyl aminobenzene-diazonium chlorozincate | 113 | Dacron felt | 26.2[a] | None | None |
|  |  | Copper | 20.0 | 20 days at 80° C. | 190* |
| p-diethylamino-benzene-diazonium chlorozincate | 117 | Dacron felt | 40.5[a] | None | None |
|  |  | Copper | 20.0 | 20 days at 80° C. | 190* |
| p-diethylamino-benzene-diazonium fluoroborate | 108 | Dacron felt | 30.8[a] | None | 120 |
|  |  | Copper | 20.0 | 1 day at 80° C. | 125 |
|  |  | Copper | 20.0 | 20 days at 80° C. | 90* |
| 2,5-diethoxy-4-morpholinobenzene diazonium chlorozincate | 120 | Copper | 20.0 | 3 days at 80° C. (sample decomposed) | — |
| 4-diethylamino-2-methylbenzene-diazonium chlorozincate | 120 | Copper | 20.0 | 3 days at 80° C. (sample decomposed) | — |
| 4-diethylamino-2-ethoxybenzene-diazonium chlorozincate | 140 | Copper | 20.0 | 24 days at 80° C. | 180 |
| 4-ethylamino-3-methylbenzene-diazonium chlorozincate | 125 | Copper | 20.0 | 2 days at 80° C. (sample decomposed) | — |
| p-amino-N-benzyl-N-ethylbenzene-diazonium chlorostannate | 160 | Copper | 20.0 | 24 days at 80° C. | 159 |
| p-dimethylaminobenzene-diazonium chlorozincate | 145 | Copper | 20.0 | 2 days at 80° C. (sample decomposed) | — |

-continued

| Diazonium Salt | Literature Decomposition Temperature (°C.) | Support Material | Concentration in Epoxy (phr)[b] | Additional Heat Treatment | Thermoparticulation Temperature (°C.) |
|---|---|---|---|---|---|
| p-chlorobenzenediazonium pentafluorophosphate | 150 | Dacron felt<br>Copper | 63.5<br>20.0 | None<br>3 days at 80° C. (sample decomposed) | 110<br>—* |

*probably due to decomposition of epoxy resin.
[a]This figure is the weight % on the Dacron felt - no resin was used.
[b]"phr" includes solvent.

| BLOCKED ISOCYANATE | | | | |
|---|---|---|---|---|
| Isocyanate Moiety | Lewis Base Moiety | Melting Point (°C.) | Aging Conditions | Thermoparticulation Temperature Range (°C.) |
| Hexamethylene Diisocyanate | Dimethylamine | 166–170 | 7 days at 60° C.<br>30 days at 80° C. | 166–171<br>166–170 |
| Toluene Diisocyanate | Mercaptobenzothiazole | 153–161 | 7 days at 60° C.<br>30 days at 80° C. | 161–165<br>164–165 |
| Toluene Diisocyanate | Diethylamine | 90–95 | 7 days at 60° C.<br>30 days at 80° C. | 154–159<br>154–157 |
| Phenyl Isocyanate | 1,3-diethylol-5,5-dimethyl hydantoin[1] | Viscous Liquid | 8 days at 60° C. | 189–195 |
| P,P'-Diphenylmethane Diisocyanate | Nitrosophenol | 179 | 8 days at 60° C. | >190° C. |
| "Mondur S"[2] | Phenol | 125–130 | 7 days at 60° C. | 190–196 |
| "Mondur SH"[3] | Phenol | 161–166 | 7 days at 60° C. | >190 |
| Hexamethylene Diisocyanate | α-Pyrrolidone | 94–96 | 7 days at 60° C. | >190 |
| Hexamethylene Diisocyanate | Phenol | 128–131 | 42 days at 60° C. | 179–189 |
| Toluene Diisocyanate | Phenol | 153–156 | 42 days at 60° C. | 170–177 |
| p,p'-Diphenylmethane Diisocyanate | Phenol | 192–194 | 42 days at 60° C. | 190–194 |
| Phenyl Isocyanate | Phenyl glycidyl ether | | overnight at 60° C. | 167 |
| Phenyl Isocyanate | Styrene oxide | | overnight at 60° C. | 172 |
| Phenyl Isocyanate | Butyl glycidyl ether | | overnight at 60° C. | 172 |
| Hexamethylene Diisocyanate | Thiophenol | | overnight at 60° C. | 141 |
| Phenyl Isocyanate | Ethylmethyl ketoxime | | overnight at 60° C. | 169–173 |
| Phenyl Isocyanate | N(2-hydroxyethyl) piperazine | | overnight at 60° C. | 180–185[4] |
| Phenyl Isocyanate | Dicyclopentenyl Alcohol | | overnight at 60° C. | 168 |
| Butyl Isocyanate | 4,4'-thiophenol | | overnight at 60° C. | 175 |
| Butyl Isocyanate | 4,4'-sulfonyl diphenol | | overnight at 60° C. | 181 |

[1]Sold by Glyco Chemicals, Inc. under the trademark "Dantocol DHE"
[2]"Mondur S" is sold by the Mobay Chemical Co. and has the structure

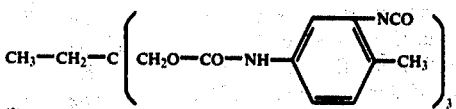

[3]"Mondur SH" is sold by the Mobay Chemical Co. and has the structure

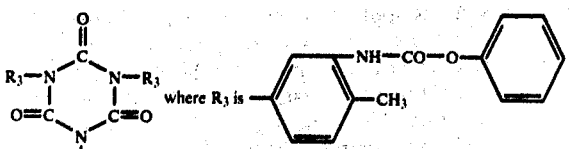

[4]Signal very strong.

| Compound | Chemical Formula | Aging Condition | Thermopaticulating Tempeature Range (°C.) |
|---|---|---|---|
| Malonic Acid | $CH_2(COOH)_2$ | 140 days at 60° C. | 132–142 |

-continued

| Compound | Chemical Formula | Aging Condition | Thermopaticulating Tempeature Range (°C.) |
|---|---|---|---|
| Methylmalonic Acid | $CH_3CH(COOH)_2$ | 140 days at 60° C. | 132–138 |
| Dimethylmalonic Acid | $(CH_3)_2C(COOH)_2$ | 180 days at 80° C. | 152–158 |
| Ethylmalonic Acid | $C_2H_5CH(COOH)_2$ | 140 days at 60° C. | 119–127 |
| Diethylmalonic Acid | $(C_2H_5)_2(COOH)_2$ | 3 days at 80° C. | 168–180 |
| Di-n-Propylmalonic Acid | $(C_3H_7)_2C(COOH)_2$ | 120 days at 80° C. | 155–160 |
| Benzylmalonic Acid | $C_6H_5CH_2CH(COOH)_2$ | 50 days at 60° C. | 143–151 |
| Phenylmalonic Acid | $C_6H_5CH(COOH)_2$ | 1 day at 60° C. | 150–157 |

The thermoparticulating temperatures given in the above tables are approximate and may vary depending on the resin used, aging time, and other factors.

In preparing the composition at least two TPC's are included which thermoparticulate at different temperatures. More than four TPC's may be included, but if this is done, resolution of the separate signals may be difficult. Preferably, the temperatures at which the TPC's thermoparticulate should be separated by at least 25° C. to provide a clear resolution of the signals. Also, the concentration of the compound which thermoparticulates at the lowest temperature should be at least 33% less than the concentration of the compound which thermoparticulates at the next higher temperature, where "concentration refers to the amount of active TPC in the total composition." Otherwise, the first compound to thermoparticulate may produce such a large, broad signal that the subsequent signals cannot be detected. Care should be taken to insure that the compounds are mutually unreactive for otherwise a reaction may occur which interferes with thermoparticulation.

If two TPC's are included in the composition, the first preferably thermoparticulates at about 125 to about 175° C. (first stage) and the second at about 175° C. to about 200° C. (second stage). Preferably, however, the composition contains three TPC's, the first preferably thermoparticulating at about 80° to about 125° C. (first stage), the second at about 125° to about 175° C. (second stage), and the third at about 175° C. to about 200° C. (third stage). If two stages are used, the first stage can serve as a warning that something may be wrong, and after the second signal is detected, the machine can be shut down or the load reduced. If three stages are used, the first can function as a warning, the second to reduce load or shut down, and the third for an automatic shut-down.

Whether to shut down or reduce load depends on a number of factors. If the second signal is received within a few hours of the first, a runaway condition may be occurring which would make a shutdown advisable. On the other hand, if the power is badly needed, a decision may be made to accept the risk of damage to the machine while operating at a reduced load. Also, after checking it may be determined that the malfunction is correctable—for example, it may be due to a reduced cooling gas pressure. Analysis of the products of thermoparticulation may also aid in deciding whether a shut-down or a reduced load is advisable since different areas of the machine can be coated with compositions containing different TPC's and the products of thermoparticulating may indicate whether the area being overheated is critical.

Consecutive signals may, of course, be due to two separate first stages from different parts of the machine. While analysis of the thermoparticulation products would determine if this is occurring, a coincidental occurrence of two first stages is not likely because overheating in these machines is fairly infrequent.

An alternative to mixing two or more TPC's into a single composition is to apply two or more separate coatings to the machine one atop the other, each containing a TPC. In this case, the resin is preferably the same in each coating to avoid problems of adherence and compatibility. As with the mixtures, the concentrations of the TPC's in the layers should be at least 33% less than the concentration of the TPC which thermoparticulates at the next higher temperature. A thickness of about 1 to about 3 mils per layer is preferred. Three layers having stages as described for the mixture would be preferred and more than four layers may make it difficult to resolve the separate signals. A layer containing a compound which thermoparticulates at a lower temperature than a compound in an adjacent layer is preferably on top of the adjacent layer so that when the layer thermoparticulates, it does not cause the adjacent layer to flake off before the compound therein has thermoparticulated. Layers may contain more than one TPC. A mixture of TPC's is preferred to a layered structure because it is less expensive to apply it to the machine. The layered structure does offer an advantage over a mixture, however, in that a physical examination or chemical analysis of the layers after thermoparticulation may indicate the maximum temperature to which the area was exposed since the lower layers may not be as severely damaged. This information is useful in determining the extent of damage to the insulation in the generator.

The composition is applied to portions of the electrical apparatus which are exposed to the gas stream. The coating formed does not function as insulation and is usually applied on top of insulation, but can also be applied to conductors. The greases are usually applied to conductors. The application may be made by painting, spraying, dipping, grease gun, or other techniques. A suitable coating thickness (after drying) is about 1/16 inch. The particles of TPC should not be covered with excessive resinous carrier as that may prevent the decomposition particles from escaping into the gas stream. After evaporation of the solvent and room temperature cure of the resinous carrier, if necessary, the apparatus is ready to be operated.

The following examples further illustrate this invention.

EXAMPLE I—A MIXTURE

The following composition was prepared:

| | Parts by Weight |
|---|---|
| Zinc acetyl acetonate ($Zn(C_5H_7O_2) \cdot 2H_2O$) | 2 |
| Dimethyl malonic acid ($(C_2H_5)_2(COOH)_2$) | 8 |
| "Krytox 240-AD" grease | 2 |
| Epoxy resin (50% solids in toluene made from 200 pbw (parts by weight) linseed fatty acids, 200 pbw styrene and 300 pbw diglycidyl ether of Bisphenol A, sold by Westinghouse Electric Corporation as "B-276" Varnish (See Example I of U.S. Pat. No. 2,909,497 for detailed description) | 10 |
| 6% solution in low-boiling hydrocarbons of cobalt naphthenate | 0.15 |
| 24% solution in low-boiling hydrocarbons of lead naphthenate | 0.38 |

The cobalt and lead naphthenate solutions were added to the epoxy resin prior to the addition of the TPC's.

A sample was prepared by brushing the above composition onto a 3 inch by 1 inch aluminum sheet to a thickness of about ⅛ to about ¼ inch. The sample was placed in an oven at 60° for 3 days to determine if it was stable and would function after aging.

The sample was placed in a stainless steel boat within a 1 inch stainless steel tube. Hydrogen was passed over the sample at a flow rate of 7 l/min. A phase-controlled temperature regulator and programmer controlled the temperature in the boat. The temperature in the boat was measured by mounting a hot junction chromel-alumel thermocouple within a small hole in the boat. The output of the thermocouple and the detector were monitored on a two-pen potentiostatic recorder. A 5° C./min. heating rate was maintained in each experiment after the insertion of the sample in the boat. The threshold temperature at which considerable particulation occurred was taken from the chart produced by the recorder. The "alarm" temperature at which considerable particulation occurred corresponded to a 50% decrease in the initial ion current of the detector (usually from 0.8 to 0.4 mA). The occurrence of particulation was detected using a Generator Condition Monitor, sold by Environment One Corporation.

Three distinct signals were obtained, one at 92° C. (due to the zinc acetyl acetonate), one at 145° C. (due to the dimethyl malonic acid), and one at 200° C. (due to the fluorinated hydrocarbon grease).

EXAMPLE II—A MIXTURE

Example I was repeated except that the concentration of zinc acetyl acetonate, dimethyl malonic acid, and "Krytox 240-AD" grease were each 4 parts by weight. A single broad signal was recorded by the monitor beginning at about 90° C. and ending at over 200° C.

EXAMPLE III—A LAYERED STRUCTURE

The following composition was prepared using the procedure of Example 1:

| | Parts by Weight |
|---|---|
| Dimethyl malonic acid | 4 |
| B-276 resin | 5 |
| 6% solution in low-boiling hydrocarbons in cobalt naphthenate | 0.08 |
| 24% solution in low-boiling hydrocarbons of lead naphthenate | 0.019 |

An aluminum foil was smeared with a layer about 2 mils thick of "Krytox 240-AD" grease and the above composition was applied to the grease to form a layer about 1/16 to about ⅛ inches thick. The layer was dried for one hour at 60° C. to form a tack-free coating.

The following composition was prepared using the procedure of Example 1:

| | Parts by Weight |
|---|---|
| Zinc acetyl acetonate | 1 |
| B-276 resin | 5 |
| 6% solution in low-boiling hydrocarbons of cobalt naphthenate | 0.08 |
| 24% soluton in low-boiling hydrocarbons of lead naphthenate | 0.019 |

The above composition was applied over the dimethyl malonic acid layer on the aluminum foil to a thickness of about 1/16 to about ⅛ inch.

The foil was aged for three days at 60° C. and tested as in Example 1. Three distinct signals were detected, one at 83° C. from the zinc acetyl acetonate, one at 140° C. from the dimethyl malonic acid, and one at 185° C. from the grease.

The thermoparticulation temperatures in this example were slightly lower than in Example 1 and the signals appeared to be slightly stronger, but the reason for these differences has not as yet been ascertained. In both examples the coatings were dark brown and heavily pitted, and appeared to be more distinctly marked than coatings containing only one TPC.

EXAMPLE IV—A LAYER

Example III was repeated except that the concentrations of dimethyl malonic acid, zinc acetyl acetonate, and "Krytox 240-AD" grease were each 4 parts by weight. A single broad signal was recorded by the monitor beginning at about 85° C. and ending at over 200° C.

EXAMPLE V—A LAYER

Example III was repeated except that the concentrations of dimethyl malonic acid and zinc acetyl acetonate were each 4 parts by weight, and the "Krytox 240-AD" grease layer was 2 mils thick. A single broad signal was recorded by the monitor beginning at about 87° C. and ending at over 200° C.

EXAMPLE VI—LAYER, REVERSED ORDER

Example III was repeated except that the zinc acetyl acetonate layer was next to the aluminum foil with a concentration of 2 parts by weight zinc acetyl acetonate, the dimethyl malonic acid layer was in the middle with a concentration of 8 parts by weight dimethyl malonic acid, and the "Krytox 240-AD" grease layer was on top with a concentration of 2 parts by weight. No signal was detected until the temperature reached 190° C., the temperature at which the grease thermoparticulates.

We claim:

1. A composition comprising at least two mutually non-reactive compounds which thermoparticulate at different temperatures between 60° and 200° C., at least 25° C. apart where the concentration of the compound which thermoparticulates at the lowest temperature is at least 33% less than the concentration of the compound which thermoparticulates at the next higher temperature, said composition including a solution of a resinous carrier curable at 60° C., stable at 60° C. when cured, and unreactive with any of said compounds which thermoparticulate, wherein the amount of said compounds total about 20 to about 250 phr and the amount of solvent in said solution is about 25 to about 75% (by weight based on the resinous carrier).

2. A composition according to claim 1 which contains two compounds, one of which thermoparticulates between about 125° and about 175° C. and the other of which thermoparticulates between about 175° and about 200° C.

3. A composition according to claim 1 which contains three compounds, one of which thermoparticulates between about 80° and about 125° C., one of which thermoparticulates between about 125° and about 175° C., and one of which thermoparticulates between about 175° and about 200° C.

4. A composition according to claim 1 wherein the amount of said compounds totals about 40 to about 60 phr and the amount of said solvent is about 45 to about 55% (by weight based on said resinous carrier).

5. A composition according to claim 1 wherein said resinous carrier is an epoxy resin.

6. A composition according to claim 5 which includes about 0.1 to about 3 phr of a drier for said epoxy resin.

7. A composition according to claim 6 which is prepared by first mixing said solution of resinous carrier and said drier and then mixing in said compounds which thermoparticulate.

8. A composition according to claim 1 where the solvent in said solution is toluene.

9. A composition according to claim 1 wherein said compounds which thermoparticulate are dispersed in said solution.

10. A composition according to claim 1 wherein said resinous carrier is air-dryable.

11. A thermoparticulating coating comprising a solid layer on a substrate which comprises a cured resinous carrier stable at 60° C. and at least two mutually unreactive compounds which thermoparticulate at different temperatures at least 25° C. apart between 60° and 200° C., where the concentration of the compound which thermoparticulates at the lower temperature is at least 33% less than the concentration of the compound which thermoparticulates at the next higher temperature, said resinous carrier being unreactive with any of said compounds which thermoparticulate, wherein the amount of said compounds totals about 20 to about 250 phr.

12. A thermal detection system for electrical apparatus cooled by a gas stream, comprising a coating according to claim 11 on a portion of said electrical apparatus exposed to said gas stream and a monitor for detecting the presence of particles in said gas stream.

13. A thermoparticulating coating on a substrate comprising at least two solid layers one atop the other, each layer comprising at least one compound which thermoparticulates at a different temperature between 60° and 200° C. where the concentration of a compound which thermoparticulates at the next lower temperature than another compound is at least 33% less than the concentration of the other compound, at least one of said layers including a resinous carrier curable at 60° C. stable when cured, and unreactive with any of said compounds which thermoparticulate, wherein the amount of each of said compounds in a resinous carrier is about 20 to about 250 phr, said layers being arranged so that no layer thermoparticulates at a higher temperature than a layer which is between it and said substrate.

14. A thermal detection system for electrical apparatus cooled by a gas stream, comprising a coating according to claim 13 on a portion of said electrical apparatus exposed to said gas stream and a monitor for detecting the presence of particles in said gas stream.

15. A method of determining the rate of temperature rise in an electrical apparatus which includes a cooling gas stream and a monitor for detecting particles in said gas stream and for emitting a signal when said particles are detected comprising:
 (A) preparing at least one composition according to claim 1;
 (B) applying at least one of said compositions to said electrical apparatus at positions exposed to said gas stream;
 (C) monitoring said gas stream to detect the presence of particulates therein; and
 (D) measuring the time between successive detections of particulates in said gas stream.

16. A method according to claim 15 including the additional last step of inspecting said apparatus visually for blistered and darkened areas, after a signal has been emitted, to locate the area of overheating.

17. A method according to claim 15 including the additional last steps of collecting a sample of said gas stream after a signal has been emitted, and analyzing said sample.

18. A method according to claim 15 including the additional last step of measuring the interval of time between signals emitted from said monitor.

19. A method of determining the rate of temperature rise in an electrical apparatus which includes a cooling gas stream and a monitor for detecting particles in said gas stream and for emitting a signal when said particles are detected comprising:
 (A) preparing at least one composition according to claim 11;
 (B) applying at least one of said compositions to said electrical apparatus at positions exposed to said gas stream;
 (C) monitoring said gas stream to detect the presence of particulates therein; and
 (D) measuring the time between successive detections of particulates in said gas stream.

20. A coating according to claim 13 wherein said compounds thermoparticulate at temperatures at least 25° C. apart.

* * * * *